United States Patent
Wang et al.

(10) Patent No.: US 11,110,445 B2
(45) Date of Patent: *Sep. 7, 2021

(54) IMMOBILIZED METALLOPORPHYRIN CATALYST AND ITS UTILIZATION IN MALEIC ACID PREPARATION

(71) Applicant: Jiangnan University, Wuxi (CN)

(72) Inventors: Haijun Wang, Wuxi (CN); Yi Huang, Wuxi (CN); Chunyan Wu, Wuxi (CN); Wenwen Yuan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 98 days.

This patent is subject to a terminal disclaimer.

(21) Appl. No.: 16/702,172

(22) Filed: Dec. 3, 2019

(65) Prior Publication Data

US 2020/0101449 A1    Apr. 2, 2020

Related U.S. Application Data

(60) Division of application No. 16/201,087, filed on Nov. 27, 2018, now Pat. No. 10,525,454, which is a
(Continued)

(30) Foreign Application Priority Data

Mar. 20, 2017    (CN) .......................... 2017101643327

(51) Int. Cl.
*B01J 31/18*    (2006.01)
*B01J 29/40*    (2006.01)
(Continued)

(52) U.S. Cl.
CPC ........... *B01J 31/1815* (2013.01); *B01J 29/14* (2013.01); *B01J 29/40* (2013.01); *B01J 29/46* (2013.01); *B01J 29/70* (2013.01); *B01J 31/183* (2013.01); *B01J 31/26* (2013.01); *B01J 37/009* (2013.01); *B01J 37/0236* (2013.01); *B01J 37/035* (2013.01); *B01J 37/04* (2013.01);
(Continued)

(58) Field of Classification Search
None
See application file for complete search history.

(56) References Cited

PUBLICATIONS

Granados et al. (RSC Advances, 4, 54960-54972 (Year: 2014).*

* cited by examiner

*Primary Examiner* — Yun Qian
(74) *Attorney, Agent, or Firm* — IPro, PLLC; Na Xu

(57) ABSTRACT

The present disclosure discloses an immobilized metalloporphyrin catalyst and its utilization in maleic acid preparation, belonging to the technical field of metalloporphyrin catalytic application. The immobilized metalloporphyrin catalyst is used for catalyzing furfural to prepare maleic acid and is good in catalytic effect, mild in reaction conditions and capable of greatly reducing the energy consumption required in the prior art. The catalyst disclosed by the present disclosure can provide a good microenvironment for a reaction, so that the yield and selectivity of maleic acid are increased; and according to a method disclosed by the present disclosure, the conversion ratio of furfural is 20.4%-95.6%, the yield of maleic acid is 10%-56.1%, and the selectivity is 43.6%-76.1%. Meanwhile, the catalyst is easy to separate and environmentally friendly and may be recycled for many times.

2 Claims, 3 Drawing Sheets

Related U.S. Application Data continuation of application No. PCT/CN2017/113868, filed on Nov. 30, 2017.

(51) Int. Cl.

| | | |
|---|---|---|
| *B01J 31/26* | (2006.01) | |
| *B01J 37/04* | (2006.01) | |
| *B01J 37/03* | (2006.01) | |
| *B01J 37/00* | (2006.01) | |
| *B01J 37/06* | (2006.01) | |
| *B01J 37/02* | (2006.01) | |
| *C07C 51/31* | (2006.01) | |
| *B01J 29/70* | (2006.01) | |
| *B01J 29/14* | (2006.01) | |
| *B01J 29/46* | (2006.01) | |

(52) U.S. Cl.
CPC ............ *B01J 37/06* (2013.01); *C07C 51/313* (2013.01); *B01J 2231/70* (2013.01); *B01J 2531/025* (2013.01); *B01J 2531/16* (2013.01); *B01J 2531/26* (2013.01); *B01J 2531/72* (2013.01); *B01J 2531/842* (2013.01); *B01J 2531/845* (2013.01); *B01J 2531/847* (2013.01)

IMMOBILIZED METALLOPORPHYRIN CATALYST AND ITS UTILIZATION IN MALEIC ACID PREPARATION

TECHNICAL FIELD

The disclosure herein relates to an immobilized metalloporphyrin catalyst and its utilization in maleic acid preparation, belonging to the technical field of metalloporphyrin catalytic application.

BACKGROUND

In the past few decades, the human society rapidly developed, the modernization level was constantly improved, meanwhile, energy and environmental problems were also getting worse. The traditional fossil energy was difficult to meet the demand of industrial development, and particularly, and the problems such as global warming, three wastes and haze brought a constant threat to the human health. Therefore, it was extremely urgent to find a clean and renewable energy to replace the traditional fossil energy. As the renewable energy most widely distributed on the earth, biomass attracts more and more attention from researchers, and there are more and more reports on the preparation of high value-added platform compounds from biomass-based raw materials, so that there is a broad prospect and significance on developing and utilizing biomass energy.

As a biomass-based C5 compound, furfural is derived from agricultural byproducts such as corn, wheat and saw dust which are widely available and renewable, and therefore, the energy reserve of the human cannot be threatened if the raw materials are utilized. Furfural may be synthesized into a plurality of platform compounds including an important high value-added intermediate, namely maleic acid which may be used as a synthesis raw material of products such as resin, a coating, an additive, a plasticizer and a drug so as to be widely applied to industrial production.

However, at present, the production route of maleic acid still adopts the way of oxidizing benzene or butane at high temperature and high pressure in the industry, the traditional fossil energy derived from petroleum is still used, and reaction conditions are relatively stringent, so that great burdens are brought for both energy and economy. In recent years, it has been constantly reported that maleic acid was synthesized by using furfural as a raw material. However, the reaction conditions of preparation methods in the reports were still relatively stringent, many reactions were required to be performed at the temperature of higher than 100° C. or the pressure of larger than 2 MPa, and the used catalysts were limited to heteropolyacid and vanadium catalysts. There is a report that $H_3PMo_{12}O_{40}+Cu(NO_3)_2$ is used as a catalytic system, furfural is catalytically oxidized at the oxygen pressure of 2 MPa, the yield of maleic acid is 49% after 14 h, although the conversion ratio of furfural is 95%, the selectivity of maleic acid is relatively low and is 52%, and the side reaction phenomenon is relatively serious. There also is a report that maleic acid is prepared by catalyzing furfural by using $H_3PMo_{12}O_{40}.xH_2O$ alone as a catalyst in a water/organic solvent double-phase system, although the selectivity of maleic acid is improved to a certain extent after the reaction lasts for 14 h, the yield is only 35%. Both yield and selectivity of maleic acid prepared in the reports are not high, and there is a serious defect that the reaction conditions are not mild enough, the oxygen pressure is relatively high, and the reaction time is also very long, so that the energy consumption caused by reactions is greatly increased.

SUMMARY

In order to overcome defects and deficiencies in the prior art, the present disclosure aims at synthesizing an immobilized metalloporphyrin catalyst with efficient catalytic capacity, which is used for converting furfural into maleic acid. The catalyst is easy to prepare, good in catalytic effect under mild reaction conditions and easy to recycle and embodies the purpose of green and sustainable development.

Ferriporphyrins with different substituent groups are firstly synthesized, although the conversion ratio of furfural may reach 90% or above under a certain condition when ferriporphyrins are directly used for a catalytic reaction, the selectivity of maleic acid is only about 50%; after ferriporphyrins are combined with molecular sieve carriers with special space structures, the yield of maleic acid is 56% and the selectivity is also up to 76% under the optimized reaction condition, meanwhile, the reaction is performed at the pressure of 1 MPa, the reaction time is only 6 h. The reaction condition is milder in comparison with that in the reports, so that the reaction energy consumption is reduced. In addition, the reaction system is heterogeneous, the catalyst can be separated by simple filtration after the reaction is ended, the immobilized metalloporphyrin catalyst separated after being cleaned and dried can also be put into use in the next time, after five cycle tests, the yield of maleic acid is still about 55%, the catalytic performance is almost unchanged. Therefore, the catalyst has the characteristics of environment friendliness, economy and practicability and has a great application prospect.

The first purpose of the present disclosure is to provide a method for preparing maleic acid by catalytically oxidizing furfural, and the method is used for producing maleic acid by carrying out a reaction of catalytically oxidizing furfural by using an immobilized metalloporphyrin catalyst, furfural serving as a substrate and oxygen serving as an oxidant.

In one embodiment, the immobilized metalloporphyrin catalyst is obtained after metalloporphyrin is combined with a molecular sieve carrier.

In one embodiment, the molecular sieve carrier is any one of MCM-41, SBA-15 and ZSM-5.

In one embodiment, the mass ratio of the catalyst to the substrate is 1:15 to 1:3.

In one embodiment, the addition amount of the catalyst is 20-100 mg of catalyst per 0.282 g of furfural.

In one embodiment, the method further comprises: separating the catalyst by filtration after ending the reaction of catalytically oxidizing furfural, carrying out cleaning and drying, and then, reusing the catalyst for the reaction of catalytically oxidizing furfural.

In one embodiment, the reaction temperature of catalytic oxidation is 70-120° C., the reaction time is 3-12 h, and the applied reaction pressure is 0.2-1.2 MPa.

In one embodiment, the reaction temperature of catalytic oxidation is 90-110° C., the reaction time is 4-5 h, and the applied reaction pressure is 0.8-1.2 MPa.

In one embodiment, the method for preparing maleic acid by catalytically oxidizing furfural specifically comprises:

(1) adding immobilized metalloporphyrin and a certain amount of solvent (water) into a polytetrafluoroethylene liner, adding a certain amount of furfural, placing the liner into a stainless steel reactor, introducing oxygen as the oxidant to carry out a reaction at the temperature of 70-120°

C. and the applied pressure of 0.2-1.2 MPa for 3-12h, after ending the reaction, cooling the reactor to the room temperature, then, slowly releasing the pressure in the reactor to normal pressure, wherein the addition amount of the catalyst is 20-100 mg; and (2) after ending the step (1), separating the catalyst by filtration, carrying out alcohol washing and drying, and then, reusing the catalyst in step (1).

In step (2), the conversion ratio of furfural is measured to be 20.4%-95.6%, the yield of maleic acid is 10%-56.1%, the selectivity is 43.6%-76.1%, and the performance of the catalyst is reduced by about 2% after the catalyst is recycled for five times.

In one embodiment, the structural formula of the metalloporphyrin is

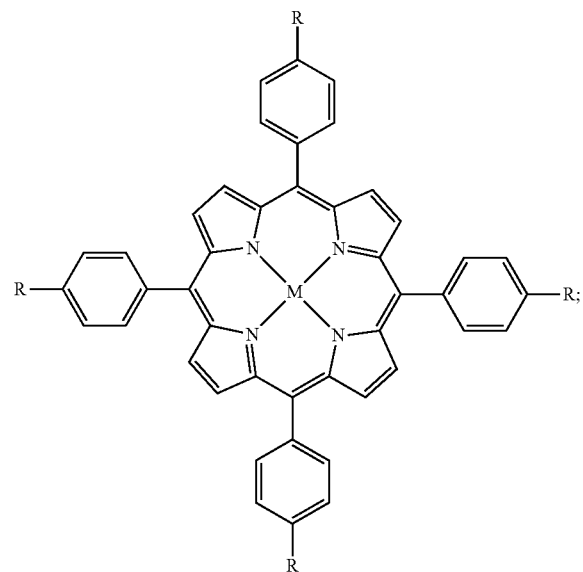

wherein R includes, but is not limited to, —H, —Br, —Cl, —F, —CH$_3$, —OCH$_3$ and —COOCH$_3$; and M represents for a metal element Fe, Mn, Co, Cu, Zn or Ni.

In one embodiment, the metalloporphyrin is substituted tetraphenylporphyrin iron, and R is —Br.

The second purpose of the present disclosure is to provide a preparation method of the immobilized metalloporphyrin catalyst, and the immobilized metalloporphyrin catalyst is obtained after metalloporphyrin is combined with a molecular sieve carrier; and the method comprises: mixing a certain number of molecular sieve carriers with a DMF solution, carrying out stirring for a period of time by heating until solid particles are uniformly dispersed, slowly and dropwise adding the DMF solution of the metalloporphyrin into the mixture, further carrying out a reaction for a period of time, carrying out cooling to the room temperature, carrying out suction filtration, cleaning filter cake by using a solvent until a filtrate is colorless, removing a porphyrin ligand relatively weakly adsorbed on the surfaces of the carriers, and carrying out drying to obtain a brown product.

In one embodiment, the molecular sieve carrier is any one of MCM-41, SBA-15 and ZSM-5.

In one embodiment, the structural formula of the metalloporphyrin is

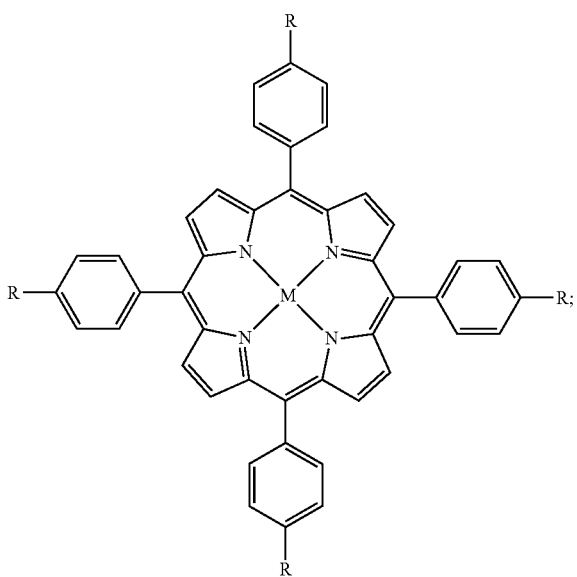

wherein R includes, but is not limited to, —H, —Br, —Cl, —F, —CH$_3$, —OCH$_3$ and —COOCH$_3$; and M represents for a metal element Fe, Mn, Co, Cu, Zn or Ni.

In one embodiment, the metalloporphyrin is substituted tetraphenylporphyrin iron, and R is —Br.

In one embodiment, the preparation of MCM-41 comprises: dissolving hexadecyl trimethyl ammonium bromide (CTAB) serving as a template into deionized water, carrying out stirring for a period of time, adding tetraethoxysilane (TEOS) into the deionized water, regulating the pH value of the solution to 10.5 by using NH$_3$.H$_2$O (28 wt %), further carrying out stirring for a period of time, transferring a gel solution into a crystallization kettle for crystallization at 105° C. for 24 h, carrying out filtration, washing, alcohol washing and drying, placing the obtained solid into a muffle furnace, and calcining to obtain an MCM-41 molecular sieve.

In one embodiment, the preparation of SBA-15 comprises: dissolving P123 serving as a template into deionized water, carrying out stirring at room temperature for a period of time, adding a 2 mol/L HCl solution into the deionized water, adding TEOS serving as a silicon source into the mixed solution, further carrying out a reaction for 22 h, transferring the mixed solution into a crystallization kettle for crystallization for 24 h, carrying out filtration, washing, alcohol washing and drying, placing the obtained solid particles into a muffle furnace, and calcining to remove the template so as to finally obtain an SBA-15 carrier.

In one embodiment, the preparation of ZSM-5 comprises: dissolving tetrapropylammonium hydroxide (TPAOH) into deionized water, stirring for a period of time, adding TEOS serving as a silicon source, regulating the pH value of the solution by using NaOH, further carrying out stirring for 24 h, adding the obtained solution into a crystallization kettle for crystallization at a certain temperature for 24 h, carrying out filtration, washing, alcohol washing and drying, and finally, placing the obtained solid into a muffle furnace, and calcining to obtain a ZSM-5 sample.

In one embodiment, the preparation of the substituted tetraphenylporphyrin iron is performed according to the following steps:

(1) the synthesis of a porphyrin ligand (T(p-R)PP): weighing a certain amount of benzaldehyde with different para-orienting groups, adding propionic acid serving as a solvent, carrying out heating in an oil bath pan until reflowing, then, slowly and dropwise adding a propionic acid solution of pyrrole into the mixed solution, carrying out a reaction for 1 h, carrying out cooling to room temperature, placing the mixed solution into a refrigerator to stand overnight, and carrying out suction filtration to obtain a crude product. The crude product is purified by using a column chromatography, and a dichloromethane/trichloromethane is used as a developing solvent, wherein R includes the substituent groups: —H, —Br, —Cl, —F, —CH$_3$, —OCH$_3$ and —COOCH$_3$.

(2) The preparation of substituted tetraphenylporphyrin iron (FeT(p-R)PP): weighing a certain number of porphyrin ligands synthesized in step (1), dissolving the porphyrin ligands into DMF, carrying out heating in an oil bath pan until reflowing, adding FeCl$_2$.4H$_2$O into the porphyrin ligands in batches, further carrying out a reaction for a period of time, removing a solvent by using a reduced-pressure distillation method, immersing the obtained solid into deionized water overnight, and carrying out suction filtration and washing until a filtrate is colorless to obtain brown ferriporphyrin.

In one embodiment, the immobilized metalloporphyrin catalyst is FeT(p-R)PP/MCM-41, FeT(p-R)PP/SBA-15 or FeT(p-R)PP/ZSM-5 obtained by immobilizing (FeT(p-R)PP) on the molecular sieve carrier MCM-41, SBA-15 or ZSM-5.

Compared with the existent technology, the immobilized metalloporphyrin catalyst has the following advantages and effects:

(1) The catalyst used in the present disclosure is immobilized metalloporphyrin which not only has a good catalytic effect for converting furfural into maleic acid, but also is mild in reaction conditions and capable of greatly reducing the energy consumption required in the existent technology.

(2) The carrier selected by the catalyst disclosed by the disclosure has a special structure and can provide a good microenvironment for a reaction, so that the yield and selectivity of maleic acid are increased. According to the method disclosed by the present disclosure, the conversion ratio of furfural is 20.4%-95.6%, the yield of maleic acid is 10%-56.1%, and the selectivity is 43.6%-76.1%; and the performance of the catalyst is reduced by about 2% after the catalyst is recycled for five times.

(3) The active site of the catalyst used in the present disclosure is metalloporphyrin which has good properties and realizes the efficient conversion from furfural into maleic acid under relatively mild reaction conditions.

(4) The immobilized metalloporphyrin catalyst disclosed by the present disclosure is heterogeneous, may be recycled and applied to the next reaction by simple filtration after the reaction is ended, still has a good catalytic effect after being cycled for many times and embodies the policy of green chemistry.

DETAILED DESCRIPTION

The present disclosure is further described below in conjunction with examples, however, the examples of the present disclosure are not limited herein.

$$\text{Selectivity} = \frac{\text{Yield}}{\text{Conversion}} \times 100\%$$

$$\text{Conversion} = \frac{\text{Moles of furfural converted}}{\text{Moles of furfural used}} \times 100\%$$

$$\text{Yield} = \frac{\text{Moles of maleic acid formed}}{\text{Moles of furfural used}} \times 100\%$$

EXAMPLE 1

(1) 50 mg of immobilized metalloporphyrin catalyst FeT(p-R)PP/SBA-15 (wherein R is —Br) is weighed and placed into a polytetrafluoroethylene liner, and the immobilized metalloporphyrin catalyst and the polytetrafluoroethylene liner are added into 4 mL of deionized water;

(2) the carrier SBA-15 in step (1) is replaced with MCM-41 and ZSM-5;

(3) 0.282 g of furfural is weighed and added into reaction systems in steps (1) and (2), the polytetrafluoroethylene liner is placed into a stainless steel reactor, heating is carried out to reach 90° C. under magnetic stirring, oxygen is introduced, 1 MPa reaction pressure is applied to carry out a reaction for 6 h, an oxygen cylinder valve is closed after the reaction is ended, the reactor is cooled to the room temperature, and then, a gas in the reactor is slowly released; and (4) 50 μL of reaction solution in step (3) is transferred by using a pipette, the volume is metered to 5 mL by using deionized water, and the yield of maleic acid is measured by using a high-performance liquid chromatograph.

Figure 1:
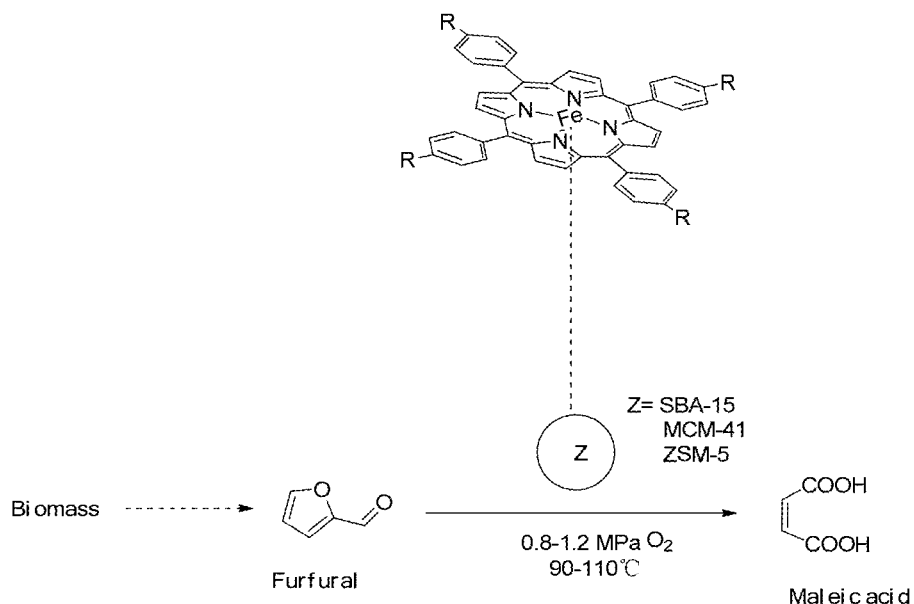
FIG. 1 is a reaction route for preparing maleic acid in the present disclosure.
Figure 2:
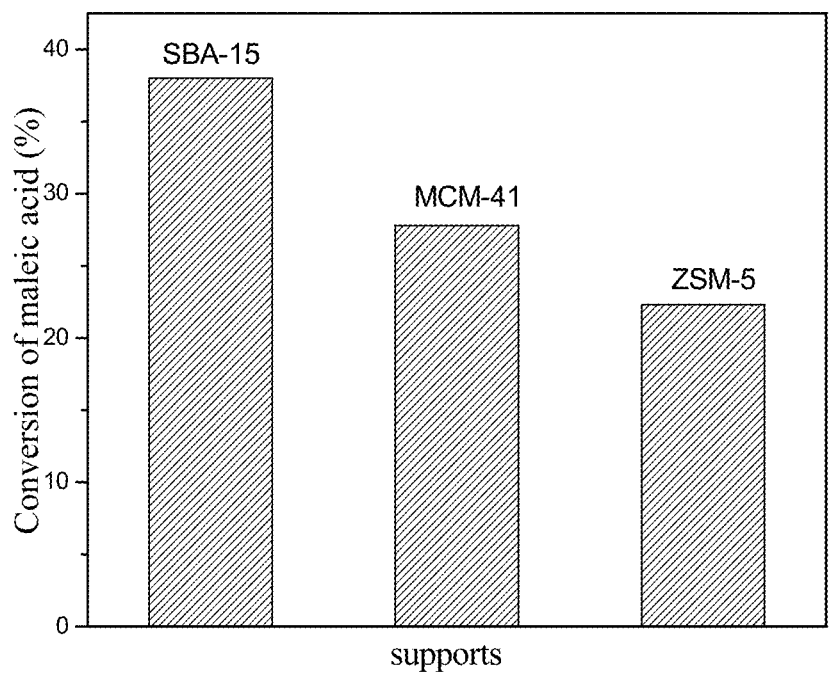
FIG. 2 is a yield diagram of furfural reactions catalyzed by using metalloporphyrin catalysts with different carrier types in Embodiment 1.

By measurement, results are shown in FIG. 2, maleic acid has the yield of 38%, 27.8% or 22.3% and the selectivity of 70.8%, 67.6% or 67% respectively when furfural is catalytically oxidized by using the catalyst prepared by taking SBA-15, MCM-41 or ZSM-5 as a carrier.

The catalytic effect is compared with the immobilized Ferriporphyrin catalysts with different substituent groups including —H, —Br, —Cl, —F, —CH$_3$, —OCH$_3$, —COOCH$_3$ and —SO$_3$Na. It is showed that the catalytic effect is best when the substituent group is —Br, and the detail is shown in the experimental data Table 1.

TABLE 1

Results for Preparing Maleic Acid by Catalytically Oxidizing Furfural by Using Immobilized Ferriporphyrins with Different Substituent Groups.

| Group | Catalyst | Selectivity (%) |
| --- | --- | --- |
| 1 | FeTPP/SBA-15 | 48.7 |
| 2 | FeT(p-Br)PP/SBA-15 | 70.8 |
| 3 | FeT(p-Cl)PP/SBA-15 | 63.5 |
| 4 | FeT(p-F)PP/SBA-15 | 52.3 |

TABLE 1-continued

Results for Preparing Maleic Acid by Catalytically Oxidizing Furfural by Using Immobilized Ferriporphyrins with Different Substituent Groups.

| Group | Catalyst | Selectivity (%) |
|---|---|---|
| 5 | FeT(p-CH$_3$)PP/SBA-15 | 62.4 |
| 6 | FeT(p-OCH$_3$)PP/SBA-15 | 63 |
| 7 | FeT(p-COOCH$_3$)PP/SBA-15 | 65.1 |
| 8 | FeT(p-SO$_3$Na)PP/SBA-15 | 56.2 |

Note:
Reaction conditions: furfural, 0.282 g; catalyst, 50 mg; H$_2$O, 4 mL; 90° C.; 6 h; and O$_2$, 1 MPa.

In addition, the disclosure tries to coordinate six metals including iron, manganese, cobalt, copper, zinc and nickel with the porphyrin ligand for a catalytic reaction, and the detail is shown in the experimental data Table 2.

TABLE 2

Experimental Results for Preparing Maleic Acid by Catalytically Oxidizing Furfural by Using Immobilized Porphyrins with Different Kinds of Metals.

| Group | Catalyst | Conversion (%) | Yield (%) | Selectivity (%) |
|---|---|---|---|---|
| 1 | FeT(p-Br)PP/SBA-15 | 53.7 | 38 | 70.8 |
| 2 | MnT(p-Br)PP/SBA-15 | 20.5 | 1.1 | 5.4 |
| 3 | CoT(p-Br)PP/SBA-15 | 33.7 | 6.2 | 18.4 |
| 4 | CuT(p-Br)PP/SBA-15 | 22 | 3.6 | 16.4 |
| 5 | ZnT(p-Br)PP/SBA-15 | 38.2 | 13.6 | 35.6 |
| 6 | NiT(p-Br)PP/SBA-15 | 19.4 | 0.8 | 4.1 |

Note:
Reaction conditions: furfural, 0.282 g; catalyst, 50 mg; H$_2$O, 4 mL; 90° C.; 6 h; and O$_2$, 1 MPa.

In addition, the catalytic activities of three immobilized metalloporphyrin catalysts with highest conversion ratios under a non-immobilization condition were studied, and the three immobilized metalloporphyrin catalysts are respectively FeT(p-Br)PP with the conversion ratio of 51.2%, ZnT(p-Br)PP with the conversion ratio of 37.5% and CoT(p-Br)PP with the conversion ratio of 30.2%. The catalytic activities of the three immobilized metalloporphyrin catalysts are slightly lower than those under an immobilization condition because mobilized metalloporphyrin has a certain catalytic activity, but the catalyst is relatively poor in stability, and is easy to oxidize and degrade; moreover, when the mobilized metalloporphyrin is in use, the reaction system is a homogeneous system, the catalyst cannot be recycled, and meanwhile, the difficulties of separating and purifying a product are also increased. However, a immobilized catalyst may be repeatedly used, and the performance of the catalyst is reduced by about 2% after the catalyst is recycled for five times.

EXAMPLE 2

(1) 50 mg of immobilized metalloporphyrin catalyst FeT(p-R)PP/SBA-15 (wherein R is —Br) is weighed and placed into a polytetrafluoroethylene liner and is added into 4 mL of deionized water;

(2) 0.282 g of furfural is weighed and added into a reaction system in step (1), the polytetrafluoroethylene liner is placed into a stainless steel reactor, heating is carried out to reach 70-120° C. under magnetic stirring, oxygen is introduced, 1 MPa reaction pressure is applied to carry out a reaction for 6 h, an oxygen cylinder valve is closed after the reaction is ended, the reactor is cooled to the room temperature, and then, a gas in the reactor is slowly released; and (3) 50 μL of reaction solution in step (2) is transferred by using a pipette, the volume is metered to 5 mL by using deionized water, and the yield of maleic acid is measured by using a high-performance liquid chromatograph.

Figure 3:
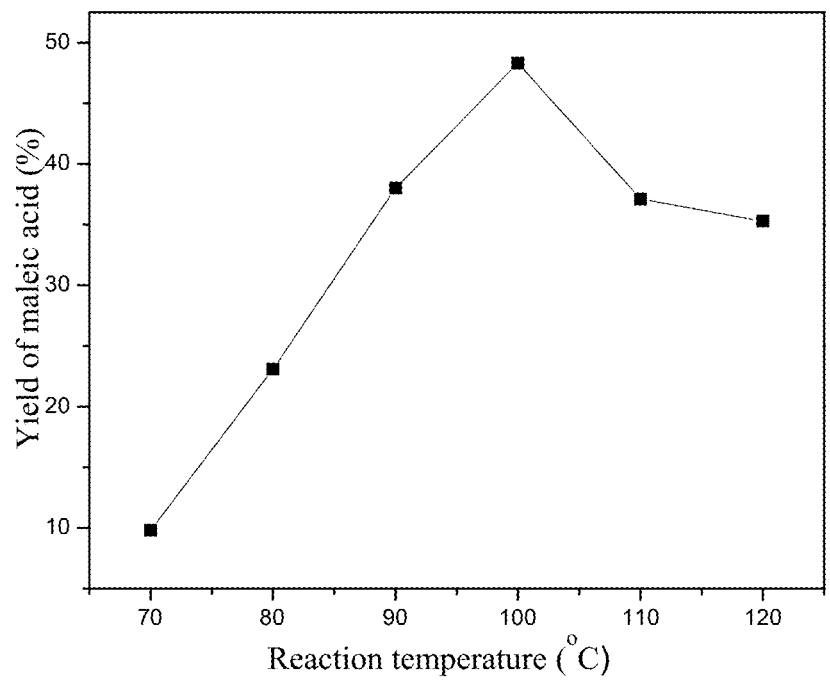
FIG. 3 is a yield diagram of furfural reactions catalyzed by using an immobilized metalloporphyrin catalyst at different temperatures in Example 2.

By measurement, results are shown in FIG. 3, maleic acid has the yield of 9.8%, 23.1%, 38%, 48.3%, 37.1% or 35.3% and the selectivity of 48%, 60.5%, 70.8%, 76.1%, 50.1% or 43.6% respectively when the reaction temperature is 70° C., 80° C., 90° C., 100° C., 110° C. or 120° C.

EXAMPLE 3

(1) 50 mg of immobilized metalloporphyrin catalyst FeT(p-R)PP/SBA-15 (wherein R is —Br) is weighed and placed into a polytetrafluoroethylene liner and is added into 4 mL of deionized water;

(2) 0.282 g of furfural is weighed and added into a reaction system in step (1), the polytetrafluoroethylene liner is placed into a stainless steel reactor, heating is carried out to reach 100° C. under magnetic stirring, oxygen is introduced, 1 MPa reaction pressure is applied to carry out a reaction for 3-8 h, an oxygen cylinder valve is closed after the reaction is ended, the reactor is cooled to the room temperature, and then, a gas in the reactor is slowly released; and (3) 50 μL of reaction solution in step (2) is transferred by using a pipette, the volume is metered to 5 mL by using deionized water, and the yield of maleic acid is measured by using a high-performance liquid chromatograph.

Figure 4:
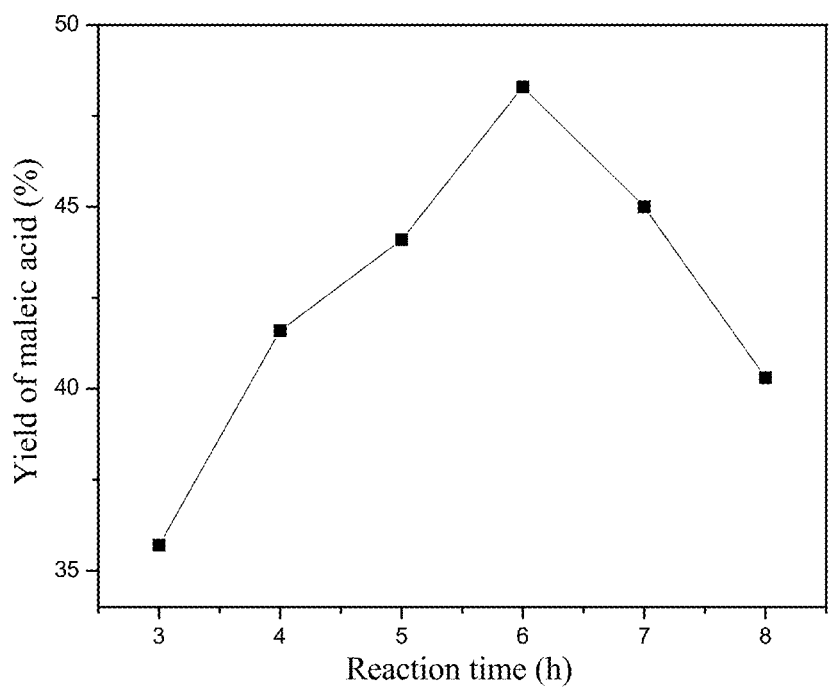
FIG. 4 is a yield diagram of furfural reactions catalyzed by using the immobilized metalloporphyrin catalyst at different times in Example 3.

By measurement, results are shown in FIG. 4, maleic acid has the yield of 35.7%, 41.6%, 44.1%, 48.3%, 45% or 40.3% and the selectivity of 76.4%, 78%, 79.5%, 76.1%, 65.7% or 49% respectively when the reaction time is 3 h, 4 h, 5 h, 6 h, 7 h or 8 h.

EXAMPLE 4

(1) 30 mg, 40 mg, 50 mg, 60 mg, 70 mg and 80 mg of immobilized metalloporphyrin catalyst FeT(p-R)PP/SBA-15 (wherein R is —Br) are weighed and placed into a polytetrafluoroethylene liner and are added into 4 mL of deionized water;

(2) 0.282 g of furfural is weighed and added into a reaction system in step (1), the polytetrafluoroethylene liner is placed into a stainless steel reactor, heating is carried out to reach 100° C. under magnetic stirring, oxygen is introduced, 1 MPa reaction pressure is applied to carry out a reaction for 6 h, an oxygen cylinder valve is closed after the reaction is ended, the reactor is cooled to the room temperature, and then, a gas in the reactor is slowly released; and (3) 50 μL of reaction solution in step (2) is transferred by using a pipette, the volume is metered to 5 mL by using deionized water, and the yield of maleic acid is measured by using a high-performance liquid chromatograph.

Figure 5:
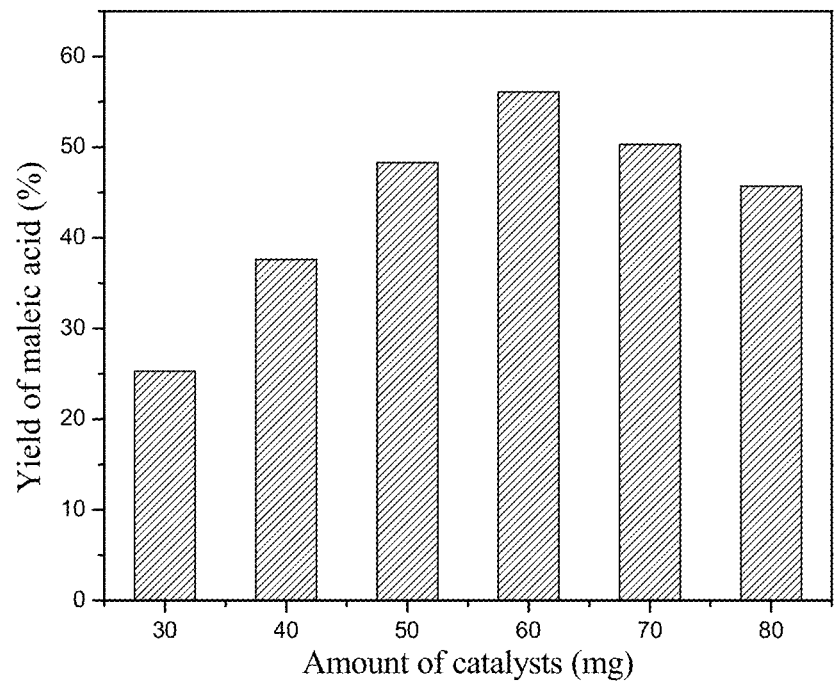
FIG. 5 is a yield diagram of furfural reactions catalyzed by using different usage amounts of immobilized metalloporphyrin catalyst in Example 4.

By measurement, results are shown in FIG. 5, maleic acid has the yield of 25.2%, 37.6%, 48.3%, 56.1%, 50.3% or 45.7% and the selectivity of 45.8%, 64.2%, 76.1%, 73.8%, 69.9% or 62% respectively when the usage amount of the catalyst is 30 mg, 40 mg, 50 mg, 60 mg, 70 mg or 80 mg.

EXAMPLE 5

(1) 60 mg of immobilized metalloporphyrin catalyst FeT(p-R)PP/SBA-15 (wherein R is —Br) is weighed and placed into a polytetrafluoroethylene liner and is added into 4 mL of deionized water;

(2) 0.282 g of furfural is weighed and added into a reaction system in step (1), the polytetrafluoroethylene liner is placed into a stainless steel reactor, heating is carried out to reach 100° C. under magnetic stirring, oxygen is introduced, 0.2 MPa, 0.4 MPa, 0.6 MPa, 0.8 MPa, 1 MPa and 1.2 MPa reaction pressures are applied to carry out a reaction for 6 h, an oxygen cylinder valve is closed after the reaction is ended, the reactor is cooled to the room temperature, and then, a gas in the reactor is slowly released; and (3) 50 μL of reaction solution in step (2) is transferred by using a pipette, the volume is metered to 5 mL by using deionized water, and the yield of maleic acid is measured by using a high-performance liquid chromatograph.

Figure 6:
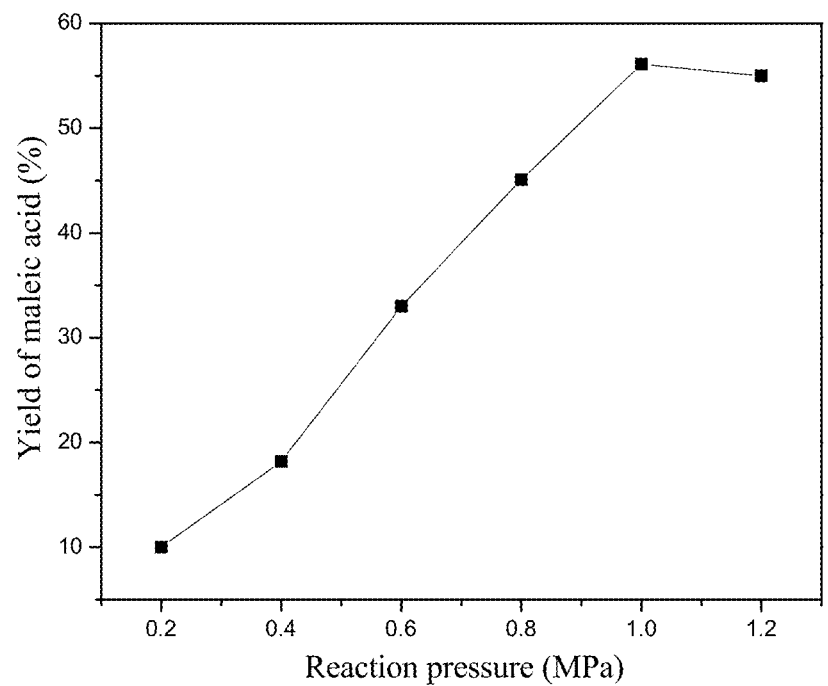
FIG. 6 is a yield diagram of furfural reactions catalyzed by using the immobilized metalloporphyrin catalyst at different reaction pressures in Example 5.

By measurement, results are shown in FIG. 6, maleic acid has the yield of 10%, 18.2%, 33%, 45.1%, 56.1% or 55% and the selectivity of 50.1%, 66.9%, 73.4%, 75.5%, 73.8% or 70.7% respectively when the reaction pressure is 0.2 MPa, 0.4 MPa, 0.6 MPa, 0.8 MPa, 1 MPa or 1.2 MPa.

After the reaction in Example 5 is ended, the catalyst under an optimal condition is separated by filtration and is cleaned and dried to be put into the optimal experimental condition in the example so as to be used for repeated calculation. By calculation, immobilized metalloporphyrin is recycled for five times, and the yield of maleic acid still reaches up to 54%.

EXAMPLE 6

Preparation of Immobilized Metalloporphyrin Catalyst

The immobilized metalloporphyrin catalyst is obtained after substituted tetraphenylporphyrin iron is combined with a molecular sieve carrier; and the method specifically comprises: mixing a certain number of molecular sieve carriers with a DMF solution, carrying out stirring for a period of time by heating until solid particles are uniformly dispersed, slowly and dropwise adding the DMF solution of metalloporphyrin into the mixture, further carrying out a reaction for a period of time, carrying out cooling to the room temperature, carrying out suction filtration, cleaning filter cake by using a solvent until a filtrate is colorless, removing a porphyrin ligand relatively weakly adsorbed on the surfaces of the carriers, and carrying out drying to obtain a brown product.

The preparation of substituted tetraphenylporphyrin iron is performed according to the following steps:

(1) The synthesis of a porphyrin ligand (T(p-R)PP): weighing a certain amount of benzaldehyde with different para-orienting groups, adding propionic acid serving as a solvent, carrying out heating in an oil bath pan until reflowing, then, slowly and dropwise adding a propionic acid solution of pyrrole into the mixed solution, carrying out a reaction for 1 h, carrying out cooling to room temperature, placing the mixed solution into a refrigerator to stand overnight, and carrying out suction filtration to obtain a crude product. The crude product is purified by using a column chromatography, and a dichloromethane/trichloromethane is used as a developing solvent, wherein R includes the substituent groups: —H, —Br, —Cl, —F, —CH$_3$, —OCH$_3$ and —COOCH$_3$.

(2) The preparation of substituted tetraphenylporphyrin iron (FeT(p-R)PP): weighing a certain number of porphyrin ligands synthesized in step (1), dissolving the porphyrin ligands into DMF, carrying out heating in an oil bath pan until reflowing, adding FeCl$_2$.4H$_2$O into the porphyrin ligands in batches, further carrying out a reaction for a period of time, removing a solvent by using a reduced-pressure distillation method, immersing the obtained solid into deionized water overnight, and carrying out suction filtration and washing until a filtrate is colorless to obtain brown ferriporphyrin.

The molecular sieve carrier is MCM-41, SBA-15 or ZSM-5, and the obtained immobilized metalloporphyrin catalysts are respectively FeT(p-R)PP/MCM-41, FeT(p-R)PP/SBA-15 and FeT(p-R)PP/ZSM-5.

The disclosure described and claimed herein is not to be limited in scope by the specific aspects herein disclosed. Any person skilled in the art can make modifications without departing from the spirit and scope of the disclosure. The scope of protection of the present disclosure should therefore be defined by the claims.

What is claimed is:

1. The method of using an immobilized metalloporphyrin catalyst, comprising oxidizing furfural with the immobilized metalloporphyrin catalyst, and obtaining maleic acid; wherein furfural serves as a substrate, oxygen serves as an oxidant and immobilized metalloporphyrin catalyst serves as a catalyst for producing maleic acid; wherein a weight ratio of amount of the immobilized metalloporphyrin catalyst to furfural is 20-100 milligrams of the immobilized metalloporphyrin catalyst per 0.282 gram of furfural; wherein the immobilized metalloporphyrin catalyst is obtained after combining metalloporphyrin with a molecular sieve carrier; wherein structural formula of the metalloporphyrin is

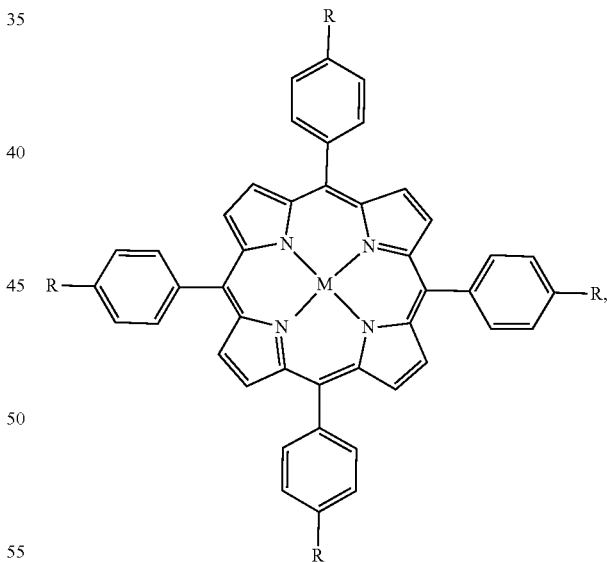

where R is selected from H, Br, Cl, F, CH$_3$, OCH$_3$, SO$_3$Na and COOCH$_3$; and M represents for a metal element Fe, Mn, Co, Cu, Zn or Ni.

2. The method according to claim 1, wherein the molecular sieve carrier is selected from a group consisting of MCM-41, SBA-15, ZSM-5, and a combination thereof.

* * * * *